US008734766B2

(12) United States Patent
Oi

(10) Patent No.: US 8,734,766 B2

(45) Date of Patent: May 27, 2014

(54) METHODS OF PRODUCING A LIP COSMETIC

(71) Applicant: The Nisshin OilliO Group, Ltd., Tokyo (JP)

(72) Inventor: Yukiko Oi, Yokohama (JP)

(73) Assignee: The Nisshin OilliO Group, Ltd., Tokyo (JP)

( * ) Notice: Subject to any disclaimer, the term of this patent is extended or adjusted under 35 U.S.C. 154(b) by 0 days.

(21) Appl. No.: 13/731,398

(22) Filed: Dec. 31, 2012

(65) Prior Publication Data

US 2013/0142744 A1 Jun. 6, 2013

Related U.S. Application Data

(63) Continuation-in-part of application No. 11/883,089, filed as application No. PCT/JP2006/301215 on Jan. 26, 2006, now abandoned.

(30) Foreign Application Priority Data

Jan. 28, 2005 (JP) ................................ 2005-021661

(51) Int. Cl.
*A61Q 1/06* (2006.01)

(52) U.S. Cl.
USPC ........................................................ 424/64

(58) Field of Classification Search
None
See application file for complete search history.

(56) References Cited

U.S. PATENT DOCUMENTS

| | | | |
|---|---|---|---|
| 3,890,358 | A | 6/1975 | Hutchison et al. |
| 5,840,943 | A | 11/1998 | Ansmann et al. |
| 7,632,957 | B2 | 12/2009 | Yamato et al. |
| 2002/0160023 | A1 | 10/2002 | Bagdi et al. |
| 2004/0191282 | A1 | 9/2004 | Fujino et al. |
| 2005/0118210 | A1 | 6/2005 | Kachi et al. |

FOREIGN PATENT DOCUMENTS

| | | | |
|---|---|---|---|
| DE | 4420516 | A1 | 12/1995 |
| EP | 1 417 955 | A1 | 5/2004 |
| EP | 1 466 586 | A1 | 10/2004 |
| EP | 1 614 411 | A1 | 1/2006 |
| JP | 49-020341 | A | 2/1974 |
| JP | 52-048613 | A | 4/1977 |
| JP | 54-109917 | A | 8/1979 |
| JP | 55-057509 | A | 4/1980 |
| JP | 56-108739 | A | 8/1981 |
| JP | 56-115740 | A | 9/1981 |
| JP | 60-033084 | B | 8/1985 |
| JP | 61-040645 | B | 9/1986 |
| JP | 62-061565 | A | 12/1987 |
| JP | 64-090025 | A | 4/1989 |
| JP | 5-331023 | A | 12/1993 |
| JP | 7-008781 | A | 1/1995 |
| JP | 7-223925 | A | 8/1995 |
| JP | 10-067889 | A | 3/1998 |
| JP | 10-120833 | A | 5/1998 |
| JP | 10-273433 | A | 10/1998 |
| JP | 2000-095666 | A | 4/2000 |
| JP | 2000-290232 | A | 10/2000 |
| JP | 2003-104843 | A | 4/2003 |
| JP | 2003-212747 | A | 7/2003 |
| JP | 2004-331573 | A | 11/2004 |
| WO | WO 02/069889 | A2 | 9/2002 |
| WO | WO 03/015741 | A1 | 2/2003 |

OTHER PUBLICATIONS

T. Ikeda: "Development of emulsion-stick based on the physiology of lips": *Fragrance*: Apr. 1992: pp. 14-21.

International Preliminary Report on Patentability (PCT/IB/308) in International Application No. PCT/JP2006/301215 dated Jul. 31, 2007 (in English).

Written Opinion of the International Searching Authority in International Application No. PCT/JP2006/301215 (in English).

Keshoshin-Jiten. Encyclopedia of Cosmetics, Maruzen, The Society of Cosmetic Chemists of Japan: p. 8: 2003.

Y. Yamato et al: "The characteristic of a new water holding material, and application to cosmetics": *Frangrance Journal*: vol. 33: pp. 53-59 (2005)(Chemical Abstracts: Abstract only).

In-Cosmetics Published online: Apr. 12, 2005: http://www.in-cosmetics.com/files/incos05__catalogue__withoutad.pdf.

Extended European Search Report dated Apr. 26, 2011 for EP06712397.6 (in English).

Database WPI: Week 200481: Thomson Scientific, London, GB;: AN 2004-817452: XP002630980: Abstract of JP 2004 331573 A: Noevir KK: Nov. 25, 2004.

European Office Action dated Dec. 23, 2011 for EP06712397.6 (in English).

*Primary Examiner* — Scott Long
*Assistant Examiner* — Sarah Alawadi
(74) *Attorney, Agent, or Firm* — Holtz Holtz Goodman & Chick PC

(57) ABSTRACT

A method of producing a lip cosmetic, comprising the steps of: (i) mixing an oligomer (ingredient (a)) produced from behenic acid, eicosane diacid, and a glycerin condensate, a polyol (ingredient (b)), and water (ingredient (c)) to prepare a solution containing ingredients (a), (b), and (c); (ii) mixing an ester oil (ingredient (d)) composed of a carboxylic acid having 2 to 36 carbon atoms and an alcohol having 1 to 36 carbon atoms, being in a liquid or paste form at ordinary temperature, and having a viscosity of 300 mPa·s or more at 25° C. and an oligomer (ingredient (e)) produced from behenic acid, eicosane diacid, and glycerin to prepare a solution containing ingredients (d) and (e); and (iii) mixing the solution containing the ingredients (a), (b), and (c) and the solution containing the ingredients (d) and (e).

3 Claims, No Drawings

METHODS OF PRODUCING A LIP COSMETIC

CROSS-REFERENCE TO RELATED APPLICATIONS

This application a Continuation-In-Part application of U.S. application Ser. No. 11/883,089 filed Jul. 26, 2007 (abandoned), which is the U.S. National Phase application of International Application No. PCT/JP2006/301215, filed Jan. 26, 2006, which further claims the priority of Japanese Application No. 2005-021661, filed Jan. 28, 2005, the entire contents of all of which are incorporated by reference herein.

TECHNICAL FIELD

The present invention relates to lip cosmetics. Specifically, the present invention relates to lip cosmetics which are excellent in the sense of use such as smoothness and adhesion upon application, excellent in moisturizing and protecting properties for lips, and excellent in long-term stability.

BACKGROUND ART

In general, skin care cosmetics are produced by emulsifying oily ingredients and aqueous ingredients using surfactants. The oily ingredients are used for adding emollient properties to the cosmetics, and the aqueous ingredients are used for adding moisturizing properties to the cosmetics. Furthermore, there is also a tendency that makeup cosmetics are required to have excellent moisture-retaining properties or water-holding properties, and various developments have been conducted. In makeup cosmetics, particularly, in lip cosmetics, the blending of water has been attempted for a long time.

For example, Patent Documents 1 to 3 disclose emulsified lip rouge including W/O type emulsifying bases blended with polyols. The lip rouge disclosed in these Patent Documents protects and moisturizes lips to some extent, but various developments have been conducted for further improving such properties.

For example, Patent Document 4 discloses a lip cosmetic including a specific oil. The lip cosmetic disclosed in this Patent Document has been mainly improved in the safety and stability. Therefore, it is required to be further improved in moisturizing properties, for example.

Patent Document 5 discloses lip balm which contains a base composed of nonaqueous ointment base, a polyol, and a nonionic surfactant and is substantially water-free. The lip balm disclosed in this Patent Document moisturizes lips to some extent, but the effect is limited because the lip balm is substantially water-free.

In Patent Document 6, an oily makeup cosmetic containing a specific oligomer is disclosed. The oily makeup cosmetic disclosed in this Patent Document can be used as, for example, lip rouge, and is excellent in gloss upon application, a touch, and preservation stability. However, it is required to be further improved in moisturizing and protecting properties.

It is understood that the addition of water to lip cosmetics as described above is useful for adding moisturizing properties to the lip cosmetics. However, W/O type emulsified lip rouge has disadvantages that the lip rouge may be readily fractured, the gloss in appearance may be lost, and the color phase may change. In O/W type emulsified lip rouge, makeup does not last for a long time and comes off quickly. In addition to such disadvantages, it is reported that lip rouge containing high moisture content, adversely, chaps lips. Therefore, O/W type emulsified lip rouge is not an optimized formula (Non-Patent Document 1).

Lip gloss is used to give lips shine. Lip cream or lip balm may be used as a base for lip rouge as a lip care product for preventing lips from drying and roughening, which are often experienced by lip rouge consumers, or may be used for protecting lips. The use of lip gloss or lip cream or balm with lip rouge takes time to do the same thing twice and also may worsen the adhesion of the lip rouge or may cause a difference between an actually perceived color and the actual lip rouge color.

[Patent Document 1] Japanese Patent Publication No. 60-33084

[Patent Document 2] Japanese Patent Publication No. 61-40645

[Patent Document 3] Japanese Patent Publication No. 62-61565

[Patent Document 4] Japanese Patent Laid-Open No. 7-223925

[Patent Document 5] Japanese Patent Laid-Open No. 2000-95666

[Patent Document 6] Japanese Patent Laid-Open No. 2003-104843

[Non-Patent Document 1] FRAGRANCE JOURNAL, published by Fragrance Journal Co., April 1992 (Heisei 4, April 15), pp. 14-21.

DISCLOSURE OF INVENTION

Problems to be Solved by the Invention

An object of the present invention is to methods of producing a lip cosmetic which are excellent in the sense of use such as smoothness and adhesion upon application, excellent in moisturizing and protecting properties for lips, and excellent in long-term stability.

Means for Solving the Problem

The present inventors have diligently studied to achieve the above-described object and have found that the object can be achieved by using specific two oligomers. Thus, the present invention has been accomplished.

The present inventors have further diligently studied to achieve the above-described object and, as a result, have found that the object can be achieved by mixing a solution containing a specific oligomer and a solution containing another specific oligomer. Thus, the present invention has been accomplished.

That is, the present invention provides the following method of producing a lip cosmetic:

A method of producing a lip cosmetic, comprising the steps of:

(i) mixing an oligomer (ingredient (a)) produced from behenic acid, eicosane diacid, and a glycerin condensate, a polyol (ingredient (b)), and water (ingredient (c)) to prepare a solution containing ingredients (a), (b), and (c);

(ii) mixing an ester oil (ingredient (d)) composed of a carboxylic acid having 2 to 36 carbon atoms and an alcohol having 1 to 36 carbon atoms, being in a liquid or paste form at ordinary temperature, and having a viscosity of 300 mPa·s or more at 25° C. and an oligomer (ingredient (e)) produced from behenic acid, eicosane diacid, and glycerin to prepare a solution containing ingredients (d) and (e); and (iii) mixing the solution containing the ingredients (a), (b), and (c) and the solution containing the ingredients (d) and (e), wherein the mass ratio ((a+b+c):(d+e)) of the total mass (a+b+c) of the ingredients (a), (b), and (c) and the total mass (d+e) of the ingredients (d) and (e) is 8:2 to 3:7;

the content of ingredient (a) is 1 to 16% by mass based on the total mass of the lip cosmetic;

the content of ingredient (b) is 18 to 40% by mass based on the total mass of the lip cosmetic;

the content of ingredient (c) is 0.1 to 10% by mass based on the total mass of the lip cosmetic;

the content of ingredient (d) is 34 to 70% by mass based on the total mass of the lip cosmetic; and the content of ingredient (e) is 0.5 to 7% by mass based on the total mass of the lip cosmetic.

The step (iii) may be performed by adding the solution containing ingredients (d) and (e) to the solution containing ingredients (a), (b), and (c) with stirring.

In the method of producing a lip cosmetic of the present invention, a branched hydrocarbon may be further mixed in the step (i), (ii), or (iii).

In the method of producing a lip cosmetic of the present invention, a dye may be further mixed in the step (i), (ii), or (iii).

Furthermore, the solution containing ingredients (a), (b), and (c) and the solution containing ingredients (d) and (e) are usually mixed with stirring.

Furthermore, ingredient (c) may be partially or fully mixed with other ingredients after the step (iii).

Advantageous Effects of the Invention

According to the present invention, lip cosmetic which are excellent in the sense of use such as smoothness and adhesion upon application, excellent in moisturizing and protecting properties for lips, and excellent in long-term stability can be provided.

BEST MODE FOR CARRYING OUT THE INVENTION

A lip cosmetic of the present invention will now be described.

The lip cosmetic of the present invention contains the following ingredients (a) to (e):

(a) an oligomer produced from behenic acid, eicosane diacid, and a glycerin condensate;

(b) a polyol;

(c) water;

(d) an ester oil which is composed of a carboxylic acid having 2 to 36 carbon atoms and an alcohol having 1 to 36 carbon atoms and which is in a liquid or paste form at ordinary temperature; and (e) an oily gelling agent.

The ingredient (a) will now be described.

The glycerin condensate for obtaining the oligomer of the ingredient (a) has an average polymerization degree of 2 or more, preferably 5 or more, and more preferably about 10. Specifically, decaglycerin is particularly preferred. In the present invention, decaglycerin, which has an average polymerization degree of about 10, is preferred, but the average polymerization degree is not limited thereto. For example, the glycerin condensate may be a mixture of those having average polymerization degrees of from 8 to 12.

The oligomer (in this description, referred to as "polyglyceryl-10 (behenate/eicosadioate)") may be produced as an esterified product by esterification reaction of behenic acid, eicosane diacid, and a glycerin condensate. The esterification reaction may be performed by, for example, (1) simultaneous esterification reaction of these three components; (2) esterification reaction of a glycerin condensate and behenic acid, and then ester exchange reaction of this esterified product and eicosane diacid; or (3) esterification reaction of a glycerin condensate and eicosane diacid, and then esterification reaction of the esterified product and behenic acid.

The oligomer used in the present invention may be produced by any one of the above-mentioned methods (1) to (3). The esterification reaction can be performed in the presence or absence of an acid, alkaline, or metal catalyst in an organic solvent and/or gas inert to the esterification reaction at 100 to 240° C. for several to twenty hours while removing the by-product water. The progress of the reaction can be monitored by measuring acid value or composition of free acids in the reaction system. The completion of the reaction can be determined by this monitoring. The reaction product of the esterification may contain unreacted glycerin condensate, behenic acid, and eicosane diacid and may further contain by-products such as fatty acids and low molecular weight glycerides. Therefore, the reaction product is purified by washing with water and removing the by-products by, for example, alkaline deacidification, and then is subjected to bleaching and deodorization.

The thus obtained oligomer is a mixture of the glycerin condensate, behenic acid, and encosane diacid which are esterified in a net-like form and has a melting point of about 50 to 80° C.

The oligomer as the ingredient (a) described above may be a commercially available one such as "Nomcort HK-P" manufactured by Nisshin OilliO Group, Ltd.

The content of the ingredient (a) is not especially limited, but is preferably 20% by mass or less, more preferably 1 to 16% by mass, more preferably 1 to 10% by mass, and most preferably 2 to 8% by mass on the basis of the total mass of the lip cosmetic. Furthermore, the content of the ingredient (a) is preferably 20% by mass or less, more preferably 2 to 20% by mass, more preferably 3 to 16% by mass, more preferably 3 to 10% by mass, and most preferably 6 to 10% by mass on the basis of the total mass (a+b+c) of the ingredients (a), (b), and (c), wherein the ingredients (b) and (c) are described below. By controlling the content of the ingredient (a) within the above-mentioned range, the lip cosmetic containing the ingredient (a) can be further improved in the sense of use.

Then, the polyols as the ingredient (b) will be described. Any alcohol having at least two hydroxyl groups in its molecule can be used as the polyol of the ingredient (b). Examples of such polyols include glycerin, diglycerin, propylene glycol, dipropylene glycol, 1,3-butylene glycol, polyethylene glycol, sorbitol, xylitol, and mannitol. The polyol may be used alone or in a combination of two or more thereof.

Among the above-mentioned examples, glycerin, diglycerin, 1,3-butylene glycol, and sorbitol are preferred as the ingredient (b), and glycerin is particularly preferred.

The content of the ingredient (b) is not especially limited, but is preferably 45% by mass or less, more preferably 18 to 40% by mass, more preferably 20 to 35% by mass, and most preferably 24 to 30% by mass on the basis of the total mass of the lip cosmetic. Furthermore, the content of the ingredient (b) is preferably 90% by mass or less, more preferably 10 to 90% by mass, more preferably 20 to 85% by mass, more preferably 40 to 85% by mass, more preferably 60 to 85% by mass, and most preferably 65 to 80% by mass on the basis of the total mass (a +b +c) of the ingredients (a), (b), and (c).

By controlling the content of the ingredient (b) within the above-mentioned range, the lip cosmetic containing the ingredient (b) can be further improved in the moisturizing properties, without being accompanied with the taste of the polyol and without giving feeling of discomfort to the user.

Next, the ingredient (c) will be described. Water as the ingredient (c) may be tap water, distilled water, or purified water. The content of the ingredient (c) is not especially limited, but is preferably 10% by mass or less, more preferably 0.1 to 10% by mass, more preferably 2 to 8% by mass, more preferably 3 to 7% by mass, and most preferably 3 to 5% by mass on the basis of the total mass of the lip cosmetic.

The lip cosmetic according to the present invention contains an oily ingredient in a gel form (gel cosmetic), and thereby excellent moisturizing properties can be achieved. By controlling the content of the ingredient (c) within the above-mentioned range, the lip cosmetic can be given in a uniform gel form, and the above-described properties can be sufficiently achieved. A lip cosmetic containing an oily ingredient in a gel form can be prepared also in a condition not containing the ingredient (c), namely, in a water-free condition. However, excellent moisturizing properties can be achieved by the presence of water. Therefore, it is preferred that water is contained in the above-mentioned range.

Next, the ingredient (d) will be described. The ingredient (d) is an ester oil composed of a carboxylic acid having 2 to 36 carbon atoms and an alcohol having 1 to 36 carbon atoms and is in a liquid or paste form at ordinary temperature (25° C.).

As the components of the ester oil, a carboxylic acid containing 1 to 6 carboxyl groups is preferred, and an alcohol containing 1 to 6 hydroxyl groups is preferred.

Examples of the ester oil composed of a carboxylic acid having 2 to 36 carbon atoms and an alcohol having 1 to 36 carbon atoms and being in a liquid or paste form at ordinary temperature (25° C.) include olive oil, castor oil, jojoba oil, mink oil, macademia nut oil, camellia oil, cetyl 2-ethylhexanoate, cetyl isoethylhexanoate (cetyl isooctanoate), isopropyl myristate, isopropyl palmitate, ethylhexyl palmitate (octyl palmitate), octyldodecyl myristate, pentaerythrityl tetraisostearate, glyceryl triisostearate, polyglyceryl-2 isostearate, polyglyceryl-2 diisostearate, polyglyceryl-2 triisostearate, polyglyceryl-2 tetraisostearate, octyldodecyl lactate, triethylhexanoin (glyceryl trioctanoate), diisostearyl malate, neopentyl glycol diethylhexanoate (neopentyl glycol dioctanoate), neopentyl glycol didecanoate, cholesteryl hydroxystearate, phytosteryl oleate, dipentaerythrityl (hydroxystearate/stearate/rosinate), dipentaerythrityl (hydroxystearate/isostearate), [glyceryl (octanoate/stearate/adipate)] glyceryl (ethylhexanoate/stearate/adipate), diglyceryl (hexyldecanoate/sebacate), glyceryl monostearate, (isostearic acid/sebacic acid) ditrimethylolpropane oligoester, ditrimethylolpropane triethylhexanoate, and erythrityl triethylhexanoate. The ingredient (d) may be used alone or in a combination of two or more thereof.

Among these examples, an ester oil having a viscosity of 300 mPa·s or more at 25° C. or being in a paste form can give excellent makeup-lasting properties to lip cosmetics and is therefore preferred as the ingredient (d). Examples of the ester oil having a viscosity of 300 mPa·s or more at 25° C. or being in a paste form include castor oil, pentaerythrityl tetraisostearate, glyceryl triisostearate, polyglyceryl-2 isostearate, polyglyceryl-2 diisostearate, polyglyceryl-2 triisostearate, polyglyceryl-2 tetraisostearate, diisostearyl malate, cholesteryl hydroxystearate, phytosteryl oleate, dipentaerythrityl (hydroxystearate/stearate/rosinate), dipentaerythrityl (hydroxystearate/isostearate), [glyceryl (octanoate/stearate/adipate)] glyceryl (ethylhexanoate/stearate/adipate), diglyceryl (hexyldecanoate/sebacate), glyceryl monostearate, (isostearic acid/sebacic acid) ditrimethylolpropane oligoester, and ditrimethylolpropane triethylhexanoate.

The lip cosmetic according to the present invention may further contain a coloring agent, as described below. Therefore, an ester oil excellent in dispersion of a coloring agent is particularly preferred. Furthermore, an ester oil having a hydroxyl group value of 5 or more can give high adhesion to lips, excellent makeup-lasting properties, and uniform appearance to lip cosmetics and, thereby, is particularly preferred. Among the above-mentioned examples, ester oils having a hydroxyl group value of 5 or more are castor oil, pentaerythrityl tetraisostearate, glyceryl triisostearate, polyglyceryl-2 diisostearate, polyglyceryl-2 triisostearate, polyglyceryl-2 tetraisostearate, diisostearyl malate, (isostearic acid/sebacic acid) ditrimethylolpropane oligoester, and ditrimethylolpropane triethylhexanoate.

The ester oil of the ingredient (d) is an ester composed of a carboxylic acid having 2 to 36 carbon atoms and an alcohol having 1 to 36 carbon atoms, and can be produced by esterification reaction of the carboxylic acid and the alcohol. The esterification reaction can be carried out by charging the carboxylic acid and the alcohol in an appropriate reaction vessel and treating them at 150 to 200° C. for about several hours to ten hours in the presence or absence of an acid, alkali, or metal catalyst in an organic solvent and/or gas which is inactive to the esterification reaction, while removing by-product water. Since unreacted materials may remain after the completion of the reaction, the unreacted materials are separated and removed by water washing, alkaline deacidification, and a known process, for example, treatment with an adsorbent such as silica gel for purification of the reaction product, and then the reaction product is subjected to bleaching and deodorization.

The ester oil of the ingredient (d) may be a commercially available one such as "Cosmol 222" (containing diisostearyl malate) manufactured by Nisshin OilliO Group, Ltd. or "Cosmol 43V" (containing polyglyceryl-2 triisostearate) manufactured by Nisshin OilliO Group, Ltd.

The content of the ingredient (d) is not especially limited, but is preferably 70% by mass or less, more preferably 30 to 70% by mass, more preferably 34 to 70% by mass, more preferably 40 to 70% by mass, more preferably 45 to 70% by mass, more preferably 45 to 65% by mass, and most preferably 45 to 60% by mass on the basis of the total mass of the lip cosmetic. By controlling the content of the ingredient (d) within the above-mentioned range, the lip cosmetic can be given in a uniform gel form, and makeup can be kept for longer time.

Next, the oily gelling agent of the ingredient (e) will be described. Any oily gelling agent which can be dissolved in the ester oil used as the ingredient (d) and can thicken or gelate the ester oil at 25° C. can be used. By blending the oily gelling agent of the ingredient (e) to a lip cosmetic, the lip cosmetic can obtain a film-forming ability and be prevented from coming off from lips.

Examples of such oily gelling agents include glyceryl (behenate/eicosadioate) (an oligomer produced from behenic acid, eicosane diacid, and glycerin), dextrin fatty acid esters, 12-hydroxystearic acid, fumy silica, sucrose fatty acid esters, metallic soap, and organic modified clay minerals. The ingredient (e) may be used alone or in a combination of two or more thereof.

For example, when the oily gelling agent is an oligomer produced from behenic acid, eicosane diacid, and glycerin, the oligomer can be produced as an esterified product of these materials. The esterification reaction can be performed as in the ingredient (a).

The thus obtained oligomer is a mixture of glycerin, behenic acid, and encosane diacid esterified in a net-like form and has a melting point of about 50 to 80° C.

The oligomer of the ingredient (e) may be a commercially available one such as "Nomcort HK-G" manufactured by Nisshin OilliO Group, Ltd.

The content of the ingredient (e) is determined depending on types of the ester oil and the oily gelling agent and is not especially limited in the range that the oily gelling agent can be dissolved in the ester oil used and thicken or gelate the ester oil at 25° C. In general, the content is preferably 0.5 to 10% by mass, more preferably 0.5 to 7% by mass, and most preferably 1 to 5% by mass on the basis of the total mass of the lip cosmetic.

In the lip cosmetic according to the present invention, the mass ratio ((a+b+c):(d+e)) of the total mass (a+b+c) of the ingredients (a), (b), and (c) and the total mass (d+e) of the ingredients (d) and (e) is not especially limited, but is preferably 8:2 to 3:7, more preferably 3:1 to 3:7, more preferably 2:1 to 3.7, and most preferably 5:5 to 3.7.

The lip cosmetic of the present invention is in a gel form as described above, and by controlling the mass ratio ((a+b+c):(d+e)) of the total mass (a+b+c) of the ingredients (a), (b), and (c) and the total mass (d+e) of the ingredients (d) and (e) within the above-mentioned range, the lip cosmetic can be given in a uniform gel form, and the effects such as moisturizing properties can be further improved.

The lip cosmetic according to the present invention may contain a coloring agent and can be used as lip rouge when containing such a coloring agent. Examples of the coloring agent include various inorganic and organic pigments such as β-carotene, iron sesquioxide, Red Nos. 2, 3, 40, 102, 104, 105, 106, 201, and 202, Yellow Nos. 4 and 5, Green No. 3, Blue Nos. 1 and 2, sodium iron chlorophylline, potassium norbixin, sodium norbixin, sodium copper chlorophylline, copper chlorophyll, titanium dioxide, xanthin, annatto pigments, alkanet dyes, aluminum, sweet potato carotene, turmeric oleoresin, shrimp color, krill color, orange color, cacao color, cacao carbon black, Japanese persimmon color, crayfish color, caramel I, caramel II, caramel III, caramel IV, carob germ color, fish scale foil, gold, silver, kusagi color, gardenia color, kooroo color, kaoliang color, cochineal color, bone carbon black, bamboo grass color, shea nut color, shikon color, sandalwood red, vegetable carbon black, sappan color, onion color, tamarind color, dunaliella carotene, paprika color, corn color, tomato color, carrot carotene, palm oil carotene, beet red, peanut color, phaffia color, grape skin color, pecan nut color, monascus color, annatto color, carthamus color, haematococcus color, marigold color, purple corn color, purple yam color, vegetable oil soot color, lac color, logwood color, red cabbage color (purple cabbage color), red rice color, red radish color, azuki color, sepia color, uguisukagura color, turmeric, elderberry juice, cowberry color, gooseberry color, cranberry color, saffron color, salmonberry color, beefsteak plant color, strawberry color, daidai extract, dark sweet cherry color, cherry color, chicory color, tea, thimbleberry color, dewberry color, layer color, hibiscus color, huckleberry color, grape juice color, black currant color, black berry color, plum color, blueberry color, boysenberry color, hop extract, whortleberry color, mulberry color, morello cherry color, mugwort extract, raspberry color, red currant color, loganberry color, and aluminum lake. The coloring agent may be used alone or in a combination of two or more thereof.

The lip cosmetic according to the present invention may contain a branched hydrocarbon. A lip cosmetic containing a branched hydrocarbon can have improved gloss and adhesive properties and also can have reduced cost. Examples of the branched hydrocarbon include isoparaffinic hydrocarbons, squalane, squalene, pristane, and α-olefin oligomers. The isoparaffinic hydrocarbons contain isobutylene as a polymer component, and examples thereof include polybutene (polybutylene), light isoparaffin, light liquid isoparaffin (isoparaffin), heavy liquid isoparaffin (hydrogenated polyisobutene), polyisobutylene (butyl-rubber), and liquid isoparaffin (liquid polyisoparaffin, hydrogenated polyisobutylene). These hydrocarbons may be purified by distillation before use. Among these examples, colorless liquid hydrocarbons are preferred. In view of giving gloss, isoparaffinic hydrocarbons are preferred, and polybutene and heavy liquid isoparaffin (hydrogenated polyisobutene) are particularly preferred. Furthermore, it is preferred that the branched hydrocarbon used has an average molecular weight of 500 to 2700. The branched hydrocarbons having such molecular weights are preferred in view of giving gloss. By containing a branched hydrocarbon having an average molecular weight in the above-mentioned range, the lip cosmetic can obtain a surface which gives comfortable touching feeling. In view of treatment in manufacturing lip cosmetics, branched hydrocarbons having average molecular weights of 800 to 1500 are further preferred.

The content of the branched hydrocarbon in a lip cosmetic according to the present invention is not especially limited, but is preferably 15% by mass or less, more preferably 2 to 15% by mass, and most preferably 5 to 12% by mass on the basis of the total mass of the lip cosmetic. By controlling the content of the branched hydrocarbon within the above-mentioned range, the lip cosmetic can be given in a uniform gel form. The total amount of the branched hydrocarbon and the ingredient (d) is preferably 70% by mass or less, more preferably 30 to 70% by mass, more preferably 40 to 70% by mass, more preferably 50 to 70% by mass, and most preferably 55 to 70% by mass on the basis of the total mass of the lip cosmetic. By controlling the total amount of the branched hydrocarbon and the ingredient (d) within the above-mentioned range, the lip cosmetic can be given in a uniform gel form.

The lip cosmetic of the present invention may further contain a perfume, an ultraviolet absorber, an antiphlogistic agent, an antiinflammatory agent, a preservative, vitamins, a fungicide, an antioxidant, a sequestering agent, a lubricant, a pH-adjuster, a flavoring, or a deodorant in the ranges that do not impair the above-described effects.

The lip cosmetic of the present invention is used as jar or stick lip rouge, lip balm, or lip gloss.

The lip cosmetic of the present invention may be produced by any process, for example, as follows:

The ingredients (a), (b), and (c) are mixed, and the resulting mixture solution is stirred at 70 to 80° C. to dissolve the ingredients (in this Description, this mixture solution containing the ingredients (a), (b), and (c) is referred to as "polyol phase"). At the same time, the ingredients (d) and (e) are stirred at 70 to 80° C. to dissolve the ingredients. The resulting mixture (in this Description, this mixture solution containing the ingredients (d) and (e) is referred to as "oil phase") is gradually added to the mixture solution containing the ingredients (a), (b), and (c) under stirring. Then, the resulting solution is cooled to about 50° C., and a dye or other additives are added thereto, according to need. The resulting mixture is cooled to room temperature to obtain a lip cosmetic of the present invention. Alternatively, the mixture solution may be poured into an appropriate container before the cooling and be cooled in the container to prepare a lip cosmetic.

EXAMPLES

The present invention will now be described in further detail with reference to examples, but is not limited to such examples. In the following examples, the terms part(s) and % denote part(s) by mass and % by mass, respectively, unless otherwise specified.

In the examples, lip cosmetics were evaluated as follows:

(1) Appearance

Lip cosmetics were observed by the naked eye and evaluated according to the following criteria:

O: having uniform appearance and being in a gel or solidified form,

X: having nonuniform appearance, being in a liquid form, or exhibiting separation.

(2) Application

Ten monitors used the lip cosmetics and evaluated them according to the following evaluation criteria. The results are shown as average of evaluation by the ten monitors.

O: being smoothly applied on lips without any problem,

X: being too hard or too soft and having difficulty in applying the lip cosmetic on lips.

(3) Makeup Lasting Quality

Ten monitors used the lip cosmetics and evaluated conditions three hours later according to the following evaluation criteria. The results are shown as average of evaluation by the ten monitors.

O: no color fading was observed by the naked eye 3 hours after the application,

X: color fading was observed by the naked eye 3 hours after the application.

(4) Prevention of Chapping of Lips

Ten monitors used the lip cosmetics for one week and evaluated conditions after one week according to the following evaluation criteria. The results are shown as average of evaluation by the ten monitors.

O: no chapping or peeling of lip skin was observed after successive application for one week, X: chapping or peeling of lip skin was observed after successive application for one week.

(5) Gloss

Ten monitors used and evaluated the lip cosmetics according to the following evaluation criteria. The results are shown as average of evaluation by the ten monitors.

O: gloss was obtained by the application on lips,

X: gloss was not obtained by the application on lips.

Examples 1 to 3

Lip cosmetics having the formulae shown in Table 1 were produced. First, the ingredients of the oil phase were weighed in a beaker at the ratio shown in Table 1 to prepare a mixture solution. This mixture solution was heated to 70° C. The unit of numerals in Table 1 is %.

At the same time, the ingredients of the polyol phase were weighed in a beaker, and the resulting mixture solution was heated to 70° C. as in the oil phase. Then, the heated polyol phase was gradually added to the oil phase over 20 min under propeller stirring at 1000 rpm. After the completion of the addition, the mixture was further stirred for 5 min. Then, the mixture was poured into a jar container and was cooled to room temperature to obtain a lip cosmetic in a gel form. The resulting lip cosmetic was subjected to the above-described evaluation. Table 2 shows the evaluation results.

TABLE 1

| | Ingredient | Example 1 | Example 2 | Example 3 |
|---|---|---|---|---|
| Polyol phase | Polyglyceryl-10 (behenate/eicosadioate) | 2 | 4 | 8 |
| | Water | 3 | 5 | 7 |
| | Glycerin | 25 | 20 | 15 |
| | Diglycerin | 0 | 8 | 10 |
| | 1,3-Butylene glycol | 0 | 3 | 10 |
| Oil phase | Glyceryl (behenate/eicosadioate) | 3 | 3 | 3 |
| | Hydrogenated polyisobutene | 10 | 0 | 12 |
| | Diisostearyl malate | 56 | 56 | 34 |
| | Red No. 104 | 1 | 1 | 1 |
| Total | | 100 | 100 | 160 |
| Polyol phase:Oil phase (mass ratio) | | 3:7 | 4:6 | 5:5 |
| Ratio (% by mass) of the amount of polyglyceryl-10 (behenate/eicosadioate) to the polyol phase | | 6.7 | 10.0 | 16.0 |

In Table 1, Polyglyceryl-10 (behenate/eicosadioate) was "Nomcort HK-P" manufactured by Nisshin OilliO Group, Ltd., glyceryl (behenate/eicosadioate) was "Nomcort HK-G" manufactured by Nisshin OilliO Group, Ltd., diisostearyl malate was "Cosmol 222" manufactured by Nisshin OilliO Group, Ltd., and hydrogenated polyisobutene was "ParLeam 18" manufactured by NOF Corp.

TABLE 2

| Evaluation item | Example 1 | Example 2 | Example 3 |
|---|---|---|---|
| Appearance | ○ | ○ | ○ |
| Ease of application | ○ | ○ | ○ |
| Makeup lasting ability | ○ | ○ | ○ |
| Lip chapping prevention | ○ | ○ | ○ |
| Gloss | ○ | ○ | ○ |

The evaluation results shown in Table 2 show that the lip cosmetics prepared in Examples 1 to 3 satisfy all the above-mentioned evaluation criteria. Furthermore, the lip cosmetics containing glyceryl-10 (behenate/eicosadioate) at a ratio to the polyol phase of 16% by mass or less satisfy all the above-mentioned evaluation criteria.

Examples 4 to 6

Lip cosmetics were produced by the same procedure as that in Examples 1 to 3, except that the formulae were those shown in Table 3. In Table 3, polyglyceryl-10 (behenate/eicosadioate), glyceryl (behenate/eicosadioate), diisostearyl malate, and hydrogenated polyisobutene were the same as those in Examples 1 to 3. The resulting lip cosmetics were subjected to the above-described evaluation. Table 4 shows the evaluation results.

TABLE 3

| | Raw material | Example 4 | Example 5 | Example 6 |
|---|---|---|---|---|
| Polyol phase | Polyglyceryl-10 (behenate/eicosadioate) | 4 | 4 | 4 |
| | Water | 2 | 5 | 10 |
| | Glycerin | 20 | 20 | 20 |
| | Diglycerin | 7 | 7 | 6 |
| | 1,3-Butylene glycol | 7 | 4 | 0 |
| Oil phase | Glyceryl (behenate/eicosadioate) | 3 | 3 | 3 |
| | Hydrogenated polyisobutene | 10 | 10 | 10 |
| | Castor oil | 10 | 10 | 10 |
| | Diisostearyl malate | 36 | 36 | 36 |
| | Yellow No. 4 | 0.5 | 0.5 | 0.5 |
| | Red No. 104 | 0.5 | 0.5 | 0.5 |
| Total | | 100 | 100 | 100 |
| Polyol phase:Oil phase (mass ratio) | | 4:6 | 4:6 | 4:6 |
| Ratio (% by mass) of the amount of polyglyceryl-10 (behenate/eicosadioate) to the polyol phase | | 10.0 | 10.0 | 10.0 |

TABLE 4

| Evaluation item | Example 4 | Example 5 | Example 6 |
|---|---|---|---|
| Appearance | ○ | ○ | ○ |
| Ease of application | ○ | ○ | ○ |
| Makeup-lasting ability | ○ | ○ | ○ |
| Lip chapping prevention | ○ | ○ | ○ |
| Gloss | ○ | ○ | ○ |

The evaluation results shown in Table 4 show that the lip cosmetics prepared in Examples 4 to 6 satisfy all the above-mentioned evaluation criteria. Furthermore, the lip cosmetics containing water in the range of 2 to 10% by mass satisfy all the above-mentioned evaluation criteria.

Examples 7 to 9 and Comparative Example 1

Lip cosmetics were produced by the same procedure as that in Examples 1 to 3, except that the formulae were those shown in Table 5. In Table 5, polyglyceryl-10 (behenate/eicosadioate), glyceryl (behenate/eicosadioate), diisostearyl malate, and hydrogenated polyisobutene were the same as those in Examples 1 to 3, and pentaerythrityl tetraisostearate was "Salacos 5418V" manufactured by Nisshin OilliO Group, Ltd. The resulting lip cosmetics were subjected to the above-described evaluation. Table 6 shows the evaluation results.

TABLE 5

| | Raw material | Example 7 | Example 8 | Example 9 | Comparative Example 1 |
|---|---|---|---|---|---|
| Polyol phase | Polyglyceryl-10 (behenate/eicosadioate) | 4 | 4 | 4 | 4 |
| | Water | 5 | 5 | 5 | 5 |
| | Glycerin | 20 | 20 | 20 | 20 |
| | Diglycerin | 7 | 7 | 7 | 7 |
| | 1,3-Butylene glycol | 4 | 4 | 4 | 4 |
| Oil phase | Glyceryl (behenate/eicosadioate) | 1 | 3 | 5 | 0 |
| | Hydrogenated polyisobutene | 10 | 10 | 10 | 10 |
| | Pentaerythrityl tetraisostearate | 10 | 10 | 10 | 10 |
| | Diisostearyl malate | 38.5 | 36.5 | 34.5 | 39.5 |
| | Red No. 202 | 0.5 | 0.5 | 0.5 | 0.5 |
| Total | | 100 | 100 | 100 | 100 |
| Polyol phase:Oil phase (mass ratio) | | 4:6 | 4:6 | 4:6 | 4:6 |
| Ratio (% by mass) of the amount of polyglyceryl-10 (behenate/eicosadioate) to the polyol phase | | 10.0 | 10.0 | 10.0 | 10.0 |

TABLE 6

| Evaluation item | Example 7 | Example 8 | Example 9 | Comparative Example 1 |
|---|---|---|---|---|
| Appearance | ○ | ○ | ○ | ○ |
| Ease of application | ○ | ○ | ○ | ○ |
| Makeup-lasting ability | ○ | ○ | ○ | X |
| Lip chapping prevention | ○ | ○ | ○ | ○ |
| Gloss | ○ | ○ | ○ | ○ |

The evaluation results shown in Table 6 show that the lip cosmetic of Comparative Example 1, which does not contain glyceryl (behenate/eicosadioate) (ingredient (e)), is inferior in makeup-lasting ability. On the other hand, the lip cosmetics prepared in Examples 7 to 9 satisfy all the above-mentioned evaluation criteria. Furthermore, the lip cosmetics containing the oily gelling agent in the range of 1 to 5% by mass satisfy all the above-mentioned evaluation criteria.

Examples 10 to 12

Lip cosmetics were produced by the same procedure as that in Examples 1 to 3, except that the formulae were those shown in Table 7. In Table 7, polyglyceryl-10 (behenate/eicosadioate), glyceryl (behenate/eicosadioate), diisostearyl malate, and hydrogenated polyisobutene were the same as those in Examples 1 to 3, and pentaerythrityl tetraisostearate was “Salacos 5418V” manufactured by Nisshin OilliO Group, Ltd. The resulting lip cosmetics were subjected to the above-described evaluation. Table 8 shows the evaluation results.

TABLE 7

| | Raw material | Example 10 | Example 11 | Example 12 |
|---|---|---|---|---|
| Polyol phase | Polyglyceryl-10 (behenate/eicosadioate) | 3 | 4 | 5 |
| | Water | 5 | 5 | 5 |
| | Glycerin | 20 | 20 | 28 |
| | Sorbitol | 0 | 7 | 7 |
| | 1,3-Butylene glycol | 2 | 4 | 5 |
| Oil phase | Glyceryl (behenate/eicosadioate) | 1 | 3 | 5 |
| | Hydrogenated polyisobutene | 10 | 10 | 10 |
| | Pentaerythrityl tetraisostearate | 0 | 10 | 10 |
| | Diisostearyl malate | 58.7 | 36.7 | 24.7 |
| | Red No. 201 | 0.3 | 0.3 | 0.3 |
| Total | | 100 | 100 | 100 |
| Polyol phase:Oil phase (mass ratio) | | 4:6 | 3:7 | 5:5 |
| Ratio (% by mass) of the amount of polyglyceryl-10 (behenate/eicosadioate) to the polyol phase | | 10.0 | 10.0 | 10.0 |

TABLE 8

| Evaluation item | Example 10 | Example 11 | Example 12 |
|---|---|---|---|
| Appearance | ○ | ○ | ○ |
| Ease of application | ○ | ○ | ○ |
| Makeup-lasting ability | ○ | ○ | ○ |
| Lip chapping prevention | ○ | ○ | ○ |
| Gloss | ○ | ○ | ○ |

The evaluation results shown in Table 8 show that the lip cosmetics prepared in Examples 10 to 12 satisfy all the above-mentioned evaluation criteria. Furthermore, the lip cosmetics containing the polyol phase and the oil phase at the mass ratio range of 3:7 to 5:5 satisfy all the above-mentioned evaluation criteria.

Example 13 and Comparative Example 2

Lip cosmetics were produced by the same procedure as that in Examples 1 to 3, except that the formulae were those shown in Table 9. The lip cosmetic in Comparative Example 2 exhibited separation and was not obtained in a uniform gel form. Therefore, it was not subjected to the evaluation.

In Table 9, polyglyceryl-10 (behenate/eicosadioate), glyceryl (behenate/eicosadioate), diisostearyl malate, and hydrogenated polyisobutene were the same as those in Examples 1 to 3, and polyglyceryl-2 triisostearate was “Cosmol 43V” manufactured by Nisshin OilliO Group, Ltd. and diisostearyl malate was “Cosmol 222” manufactured by Nisshin OilliO Group, Ltd. The resulting lip cosmetics were subjected to the above-described evaluation. Table 10 shows the evaluation results.

TABLE 9

| | Raw material | Example 13 | Comparative Example 2 |
|---|---|---|---|
| Polyol phase | Polyglyceryl-10 (behenate/eicosadioate) | 4 | 4 |
| | Water | 5 | 5 |
| | Glycerin | 24 | 24 |
| | Diglycerin | 7 | 7 |
| Oil phase | Glyceryl (behenate/eicosadioate) | 3 | 3 |
| | Hydrogenated polyisobutene | 10 | 56 |
| | Polyglycery1-2 triisostearate | 46 | 0 |
| | Diisostearyl malate | 0 | 0 |
| | Red No. 104 | 1 | 1 |
| Total | | 100 | 100 |
| Polyol phase:Oil phase (mass ratio) | | 4:6 | 4:6 |
| Ratio (% by mass) of the amount of polyglyceryl-10 (behenate/eicosadioate) to the polyol phase | | 10.0 | 10.0 |

TABLE 10

| Evaluation Item | Example 13 | Comparative Example 2 |
|---|---|---|
| Appearance | ○ | — |
| Ease of application | ○ | — |
| Makeup-lasting ability | ○ | — |
| Lip chapping prevention | ○ | — |
| Gloss | ○ | — |

The evaluation results shown in Table 10 show that the lip cosmetic produced in Examples 13 satisfies all the above-mentioned evaluation criteria. However, the lip cosmetic of Comparative Example 2, which does not contain the ester oil of the ingredient (d), exhibits separation and is not given in a uniform gel form. Therefore, it is confirmed that the ester oil in the ingredient (d) is an essential ingredient of the lip cosmetic according to the present invention.

The invention claimed is:

1. A method of producing a lip cosmetic having smoothness and adhesion upon application, moisturizing and protecting properties, and long-term stability, the method comprising the steps of:

(i) mixing an oligomer (ingredient (a)) produced from behenic acid, eicosane diacid, and a glycerin condensate, a polyol (ingredient (b)), and water (ingredient (c)) to prepare a solution containing ingredients (a), (b), and (c);

(ii) mixing one or more ester oils selected from the group consisting of castor oil, pentaerythrityl tetraisostearate, polyglycerol-2 triisostearate and diisostearyl malate (ingredient (d)) with an oligomer (ingredient (e)) produced from behenic acid, eicosane diacid, and glycerin to prepare a solution containing ingredients (d) and (e); and (iii) gradually adding the solution containing the ingredients (a), (b), and (c) to the solution containing the ingredients (d) and (e), with stirring, wherein the mass ratio ((a+b+c):(d+e)) of the total mass (a+b+c) of the ingredients (a), (b), and (c) and the total mass (d+e) of the ingredients (d) and (e) is 8:2 to 3:7;

the content of ingredient (a) is 1 to 16% by mass based on the total mass of the lip cosmetic;

the content of ingredient (b) is 18 to 40% by mass based on the total mass of the lip cosmetic;

the content of ingredient (c) is 2 to 10% by mass based on the total mass of the lip cosmetic;

the content of ingredient (d) is 34 to 70% by mass based on the total mass of the lip cosmetic; and the content of ingredient (e) is 0.5 to 7% by mass based on the total mass of the lip cosmetic.

2. The method of producing a lip cosmetic according to claim 1, wherein a branched hydrocarbon is further mixed in the step (ii).

3. The method of producing a lip cosmetic according to claim 1, wherein a dye is further mixed in the step (ii).

* * * * *